United States Patent [19]
Föry et al.

[11] 3,933,881
[45] Jan. 20, 1976

[54] PROCESS FOR THE MANUFACTURE OF β-CHLOROETHYL-METHYL-DICHLOROSILANE

[75] Inventors: Werner Föry, Basel; Hermann Kny, Fullinsdorf, both of Switzerland

[73] Assignee: Ciba-Geigy Corporation, Ardsley, N.Y.

[22] Filed: Dec. 12, 1974

[21] Appl. No.: 532,143

[30] Foreign Application Priority Data
Dec. 15, 1973 Switzerland.................. 17556/73

[52] U.S. Cl. ............................ 260/448.2 E; 203/6
[51] Int. Cl.² ........................................ C07F 7/12
[58] Field of Search ............................ 260/448.2 E

[56] References Cited
UNITED STATES PATENTS
3,801,614   4/1974   Lohmann et al............. 260/448.2 E Primary Examiner—Paul F. Shaver
Attorney, Agent, or Firm—Frederick H. Rabin

[57] ABSTRACT

A process for the manufacture of β-chloroethyl-methyl-dichlorosilane by addition of HCl to methylvinyl-dichlorosilane in the presence of $AlCl_3$ and distilling off the resultant end product from the reaction mixture, wherein the isolation of the β-chloroethyl-methyl-dichlorosilane by distillation is effected in the presence of at least 1 mole of alkali metal chloride or of ammonium chloride, relative to $AlCl_3$, at a bath temperature above 30°C in vacuo.

5 Claims, No Drawings

PROCESS FOR THE MANUFACTURE OF β-CHLOROETHYL-METHYL-DICHLOROSILANE

The present invention provides an improved process for the economic manufacture of β-chloroethyl-methyl-dichlorosilane.

This compound of the formula

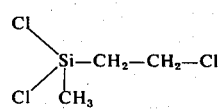

has recently acquired great importance, in particular as starting material for the manufacture of plant growth regulators, for example agents that stimulate fruit abscission and latex flow, belonging to the class of β-chloroethyl-methyl-silanes which are variously substituted at the Si atom (DOS 2,239,412 and DOS 2,309,762).

The manufacture of this compound has been carried out hitherto in analogous manner to the manufacture of β-chloroethyl-trichlorosilane [Ind. Eng. Chem. 45 (1953), 367] by addition of HCl in the presence of Lewis acids, in particular aluminium chloride, to methylvinyl-dichlorosilane [$Cl_2(CH_3)-Si-CH=CH_2$] and distilling off the resultant β-chloroethyl-methyl-dichlorosilane, which is highly unstable in the reaction mixture, at bath temperatures in the region of 15°C in a high vacuum and with intensive cooling of the receiver (DOS 2,239,412, Ex. 6).

In contrast to β-chloroethyl-trichlorosilane, which can be distilled off from the reaction mixture containing $AlCl_3$ without difficulty and without decomposition at room temperature, the β-chloroethyl-methyl-dichlorosilane which is formed in the same way is so susceptible and unstable that it has only been possible to isolate it on a laboratory scale by distillation from the reaction mixture containing $AlCl_3$ at bath temperatures below 15°C in a high vacuum (0.1 Torr) by dint of time-consuming petty work with intensive cooling of the receiver. The compound decomposes in the presence of $AlCl_3$ even at temperatures of 10°-20°C to form the starting product or methyl-trichlorosilane and ethylene. Manufacture on an industrial scale is therefore not possible under these conditions for the isolation by distillation.

The surprising discovery has now been made that these difficulties can be avoided and the distillation accomplished in an economic manner by carrying out the distillation to isolate the important intermediate in the presence of amounts of an alkali metal chloride or ammonium chloride that deactivate the $AlCl_3$.

The process according to the invention for the manufacture of β-chloroethyl-methyl-dichlorosilane by addition of HCl to methyl-vinyl-dichlorosilane in the presence of $AlCl_3$ and distilling off the resultant end product from the reaction mixture consists in carrying out this distillation in the presence of at least 1 mole of alkali metal chloride or ammonium chloride, relative to $AlCl_3$, at a bath temperature above 30°C in vacuo.

The use of double salts of aluminium halides such as $AlCl_3$ with alkali metal chlorides as condensation agent for Friedel-Crafts reactions is known [G.A. Olah, "Friedel-Crafts and Related Reactions," Vol. 1 (1963), Interscience Publishers], but has nothing to do with the idea of the present invention which has for its object the deactivation of $AlCl_3$ before the isolation of an unstable end product by distillation, that is to say which solves a totally different problem of silane chemistry and one which has hitherto not yet arisen.

It is of course possible to add the alkali metal chloride or the ammonium chloride right at the start, i.e. before the HCl addition, to the $AlCl_3$, whereby possibly a double salt is formed, and in this way the HCl addition can also be carried out. The mixture of $AlCl_3$ and the stabilising alkali metal chloride or ammonium chloride or the double salt is then already present in the reaction mixture during the isolation of the resultant β-chloroethyl-methyl-dichlorosilane by distillation. However, the presence of alkali metal chloride or ammonium chloride or of a double salt with $AlCl_3$ in the reaction mixture before the start of the distillation is essential.

Examples of alkali metal chlorides which can be added are NaCl, LiCl and KCl; but sodium chloride is preferred.

The minimum molar ratio of $AlCl_3:NaCl$ is 1:1. Preferred molar ratios of $AlCl_3:NaCl$ are from 1:1 to 1:2, in particular about 1:1.1 in view of the yields to be obtained, in the event of the alkali metal chloride being added before the HCl addition.

If, on the other hand, the alkali metal chloride is not added until before the distillation, it is also possible to add 2 and more moles, i.e. any desired surplus thereof, relative to to the $AlCl_3$, without detriment to the yields.

Conventional distillation apparatus with a vacuum of 15–30 Torr and bath temperatures between 40° and 90°C are used to isolate the β-chloroethyl-methyl-dichlorosilane from the reaction mixture. It is consequently possible to manufacture the end product under conditions which are feasible on an industrial scale in respect of the apparatus employed.

The following Examples will serve to illustrate the invention.

EXAMPLE 1

A mixture of 105.8 parts by weight of methylvinyldichlorosilane and 2.5 parts by weight of anhydrous $AlCl_3$ is cooled to 0°C. At this temperature, dry hydrochloric acid is passed in over the course of 1½ hours. After the uptake of HCl is terminated, 10 parts by weight (9 moles, relative to to $AlCl_3$) of anhydrous NaCl are added at 0°C and the mixture is stirred for 10 minutes at this temperature. The mixture is warmed to room temperature and stirred for 1 hour thereat, in the course of which the onset of an exothermic reaction is controlled by cooling from time to time. The resultant end product is distilled direct from the reaction vessel in a conventional vacuum distillation apparatus at a bath temperature of 80°C. Yields: 96 parts by weight (71.5% yield) of the known 2-chloroethyl-(methyldichloro)silane with a boiling point of 50°-52°C/18 Torr.

|    | Calculated: | found: |
|----|-------------|--------|
| C  | 20,29       | 20,9   |
| H  | 3,97        | 4,1    |
| Cl | 59,91       | 59,9   |
| Si | 15,82       | 16.0   |

EXAMPLE 2

A mixture of 113.8 parts by weight of methylvinyl-dichloro-silane, 2.5 parts by weight of anhydrous $AlCl_3$ and 1.1 parts by weight of anhydrous NaCl (molar ratio 1:1) is cooled to 0°-5°C. At this temperature, dry hydrochloric acid is passed in over the course of 1½ hours. After termination of the uptake of HCl, the product is distilled direct from the reaction vessel as in Example 1. Yield: 93 parts by weight (64.5% yield) of 2-chloro-ehtyl-(methyl-dichloro)silane.

EXAMPLE 3

The procedure of Example 2 is carried out, except that 2.2 parts by weight of NaCl (molar ratio 1:2) are used. Yield: 73.1 parts by weight of 2-chloromethyl-(methyl-dichloro) silane (51% yield). It is evident that a NaCl surplus - if this is already present before the HC1 addition - does not increase the yield.

We claim:

1. A process for the manufacture of β-chloroethyl-methyl-dichlorosilane by addition of HCl to methylvinyl-dichlorosilane in the presence of $AlCl_3$ and distilling off the resultant end product from the reaction mixture, wherein the isolation of the β-chloroethyl-methyl-dichlorosilane by distillation is effected in the presence of at least 1 mole of alkali metal chloride or of ammonium chloride, relative to $AlCl_3$, at a bath temperature above 30°C in vacuo.

2. A process according to claim 1, wherein the isolation of the end product from the reaction mixture by distillation is carried out in the presence of sodium chloride.

3. A process according to claim 1, wherein 1 to at most 2 moles of NaCl, relative to the amount of $AlCl_3$, are added before the HCl addition to the starting mixture containing the aluminium chloride, and wherein both the HCl addition to the methylvinyl-dichlorosilane and the isolation of the resultant β-chloroethyl-methyl-dichlorosilane from the reaction mixture by distillation are effected in the presence of this aluminium chloride/sodium chloride mixture.

4. A process according to claim 1, wherein the HCl addition is effected with aluminium chloride alone and wherein subsequently, but before the isolation of the end product by distillation, at least 1 mole of NaCl, relative to the aluminium chloride used, is added to the reaction mixture.

5. A process according to claim 1, wherein the isolation is effected with a conventional distillation apparatus at bath temperatures between 40° and 90°C and pressures between 15 and 30 Torr.

\* \* \* \* \*